(12) United States Patent
Killebrew et al.

(10) Patent No.: US 11,680,032 B2
(45) Date of Patent: Jun. 20, 2023

(54) ALCOHOLS PRODUCTION

(71) Applicant: SCION Holdings LLC, Houston, TX (US)

(72) Inventors: Kyle Killebrew, Houston, TX (US); Samuel Livingston Lane, Seabrook, TX (US)

(73) Assignee: SCION Holdings LLC, Houston, TX (US)

( * ) Notice: Subject to any disclaimer, the term of this patent is extended or adjusted under 35 U.S.C. 154(b) by 0 days.

(21) Appl. No.: 17/246,580

(22) Filed: Apr. 30, 2021

(65) Prior Publication Data

US 2021/0380516 A1 Dec. 9, 2021
US 2022/0315515 A2 Oct. 6, 2022
US 2023/0021297 A9 Jan. 19, 2023

Related U.S. Application Data

(60) Provisional application No. 63/035,073, filed on Jun. 5, 2020.

(51) Int. Cl.
| | | |
|---|---|---|
| C07C 45/50 | (2006.01) | |
| B01J 31/00 | (2006.01) | |
| B01J 31/24 | (2006.01) | |
| B01J 31/18 | (2006.01) | |
| C07C 5/25 | (2006.01) | |

(52) U.S. Cl.
CPC ........... *C07C 45/505* (2013.01); *B01J 31/185* (2013.01); *B01J 31/2404* (2013.01); *B01J 31/2495* (2013.01); *C07C 5/2593* (2013.01); *B01J 2231/321* (2013.01); *B01J 2231/52* (2013.01); *B01J 2531/822* (2013.01); *C07C 2531/24* (2013.01)

(58) Field of Classification Search
CPC .... C07C 45/505; B01J 31/185; B01J 31/2404
See application file for complete search history.

(56) References Cited

U.S. PATENT DOCUMENTS

| | | |
|---|---|---|
| 3,480,556 A | 11/1969 | De Witt et al. |
| 4,336,032 A | 6/1982 | Kupka et al. |
| 4,443,638 A * | 4/1984 | Yates ............... C07C 29/141 |
| | | 568/454 |
| 4,528,245 A | 7/1985 | Jobbins |
| 4,642,388 A | 2/1987 | Young |
| 4,670,606 A | 6/1987 | Romano et al. |
| 4,922,028 A | 5/1990 | Oswald et al. |
| 4,940,574 A | 7/1990 | Kaplan |
| 5,030,774 A | 7/1991 | Oswald et al. |
| 5,364,552 A | 11/1994 | Merz et al. |
| 5,481,044 A | 1/1996 | Weber et al. |
| 5,574,084 A | 11/1996 | Peacock |
| 5,789,367 A | 8/1998 | Blokzijl et al. |
| 5,833,719 A | 11/1998 | Francois et al. |
| 5,849,960 A | 12/1998 | Singleton et al. |
| 5,919,987 A | 7/1999 | Kneuper et al. |
| 6,225,507 B1 | 5/2001 | Giessler et al. |
| 6,448,213 B1 | 9/2002 | Willman |
| 6,500,991 B2 | 12/2002 | Wiese et al. |
| 6,514,926 B1 | 2/2003 | Kott et al. |
| 6,653,514 B1 | 11/2003 | Murray et al. |
| 6,765,106 B2 | 7/2004 | Fenouil et al. |
| 6,770,722 B2 | 8/2004 | Weitzel et al. |
| 6,849,589 B2 | 2/2005 | Liu |
| 7,022,889 B2 | 4/2006 | Gillespie et al. |
| 7,074,395 B2 | 7/2006 | Milbradt et al. |
| 7,183,446 B2 | 2/2007 | Zeller et al. |
| 7,223,898 B2 | 5/2007 | Rice |
| 7,232,931 B2 | 6/2007 | Toetsch et al. |
| 7,250,468 B2 | 7/2007 | Harzschel et al. |
| 7,300,966 B2 | 11/2007 | Breitscheidel et al. |
| 7,335,802 B2 | 2/2008 | Ayoub et al. |
| 7,365,234 B2 | 4/2008 | Subramaniam et al. |
| 7,541,414 B2 | 6/2009 | Lion |
| 7,615,645 B2 | 11/2009 | Volland et al. |
| 7,863,487 B2 | 1/2011 | Eisenschmid et al. |
| 7,906,688 B2 | 3/2011 | Brammer et al. |
| 7,956,113 B2 | 6/2011 | Killat et al. |
| 8,178,729 B2 | 5/2012 | Karvinen et al. |
| 8,334,323 B2 | 12/2012 | Varineau et al. |
| 8,586,686 B2 | 11/2013 | Zecha et al. |
| 8,692,027 B2 | 4/2014 | Norman et al. |
| 8,901,058 B2 | 12/2014 | Evers et al. |
| 9,493,725 B2 | 11/2016 | Vinson et al. |
| 9,493,726 B2 | 11/2016 | Vinson et al. |
| 9,828,565 B2 | 11/2017 | Sharko |
| 9,828,573 B2 | 11/2017 | Sharko |

(Continued)

FOREIGN PATENT DOCUMENTS

| | | |
|---|---|---|
| CN | 101768060 B | 7/2013 |
| CN | 106496541 A | 3/2017 |

(Continued)

OTHER PUBLICATIONS

Hanson, Brian E. Hydroformylation of 1-Hexene Utilizing Homogeneous Rhodium Catalysts. Journal of Chemical Education, vol. 64 (11), 928-930. (Year: 1987).*
PCT International Search Report, Application No. PCT/US2021/035772, ISA (dated Oct. 26, 2021).
PCT International Search Report, Application No. PCT/US2021/034189, ISA (dated Sep. 24, 2021).
PCT International Search Report, Application No. PCT/US2021/035169, ISA (dated Aug. 31, 2021).
PCT International Search Report, Application No. PCT/US2021/030341, ISA (dated Aug. 3, 2021).

(Continued)

*Primary Examiner* — Sikarl A Witherspoon

(74) *Attorney, Agent, or Firm* — Wright IP & International Law; Eric G. Wright

(57) ABSTRACT

A process for producing branched alcohols through isomerization, hydroformylation and hydrogenation.

19 Claims, 9 Drawing Sheets

(56) References Cited

U.S. PATENT DOCUMENTS

| | | |
|---|---|---|
| 9,890,105 B2 | 2/2018 | Krill et al. |
| 9,944,773 B2 | 4/2018 | Alidedeoglu et al. |
| 10,196,336 B2 | 2/2019 | Elowe et al. |
| 10,233,467 B2 | 3/2019 | Huo et al. |
| 10,501,392 B2 | 12/2019 | Fridag et al. |
| 10,562,833 B2 | 2/2020 | Fridag et al. |
| 10,577,297 B2 | 3/2020 | Fridag et al. |
| 10,676,762 B2 | 6/2020 | Huo et al. |
| 10,766,833 B2 | 9/2020 | Zhang |
| 2002/0183567 A1 | 12/2002 | Fenouil et al. |
| 2004/0030200 A1 | 2/2004 | Zeller et al. |
| 2005/0107637 A1 | 5/2005 | Gerlach et al. |
| 2007/0260021 A1 | 11/2007 | Lumpp |
| 2010/0261628 A1 | 10/2010 | Scherer et al. |
| 2012/0010423 A1 | 1/2012 | Scheibel et al. |
| 2012/0149629 A1 | 6/2012 | Dahms et al. |
| 2013/0237726 A1 | 9/2013 | Krokoszinski et al. |
| 2013/0324767 A1 | 12/2013 | Norman et al. |
| 2017/0051195 A1 | 2/2017 | Vanzin et al. |
| 2017/0355656 A1 | 12/2017 | Brammer et al. |
| 2019/0337866 A1 | 11/2019 | Zhang |
| 2021/0078925 A1 | 3/2021 | Zuend et al. |

FOREIGN PATENT DOCUMENTS

| | | |
|---|---|---|
| EP | 1680387 B1 | 9/2007 |
| EP | 1678109 B1 | 1/2011 |
| WO | 9314057 | 7/1993 |
| WO | 199739091 | 10/1997 |
| WO | 9823566 A1 | 6/1998 |
| WO | 2005009934 A2 | 2/2005 |
| WO | 2005037753 A1 | 4/2005 |
| WO | 2017223271 A1 | 12/2017 |
| WO | 2020057878 A1 | 3/2020 |

OTHER PUBLICATIONS

Wu et al., "Branched Alkyl Alcohol Propoxylated Sulfate Surfactants for Improved Oil Recovery", Tenside Surf. Det. 47 (2010) 3.

Mathivet et al., "Perfluorooctyl Substituted Triphenylphosphites as Ligands for Hydroformylation of Higher Olefins in Fluorocarbon/Hydrocarbon Biphasic Medium", C. R. Chimie 5, 417-424 (2002).

International Preliminary Report on Patentability, Application No. PCT/US2021/035169, IPEA/US (dated Apr. 11, 2022).

International Preliminary Report on Patentability, Application No. PCT/US2021/030341, IPEA/US (dated Apr. 7, 2022).

Baoxin Zhang et al., "Hydroformylation", ChemTexts 8:2 (2022), Springer Nature (Dec. 2, 2021), https://doi.org/10.1007/s40828-021-00154-x.

Richard Tudor et al., "Industrial Low Pressure Hydroformylation: Forty-Five Years of Progress for the LP Oxo(SM) Process", Johnson Matthey Technol. Rev., 61(3), 246-256 (2017), https://doi.org/10.1595/205651317X695875.

Robert Franke et al., "Applied Hydroformylation", Chem. Rev., 112, 5675-5732 (2012), ACS Publications (Aug. 31, 2012), https://dx.doi.org/10.1021/cr3001803.

Jeffrey J. Scheibel, "The Evolution of Anionic Surfactant Technology to Meet the Requirements of the Laundry Detergent Industry", AOCS Press, Journal of Surfactants and Detergents, 7(4), 319 (Oct. 2004).

"Catalysis by Metal Complexes: Rhodium Catalyzed Hydroformylation", Kluwer Academic Publishers (Piet W.N.M. van Leeuwen & Carmen Claver eds.), vol. 22 (2000).

Examination Report, Application No. 202227065719, IPI (dated Jan. 17, 2023).

PCT International Preliminary Report On Patentability, Application No. PCT/US2021/035772, IPEA (dated Dec. 9, 2022).

PCT International Search Report, Application No. PCT/US2022/031481, ISA (dated Aug. 24, 2022).

PCT International Preliminary Report On Patentability, Application No. PCT/US2021/063934, IPEA (dated Jul. 22, 2022).

PCT International Search Report, Application No. PCT/US2021/063934, ISA (dated May 11, 2022).

PCT International Preliminary Report On Patentability, Application No. PCT/US2021/034189, IPEA (dated May 9, 2022).

* cited by examiner

SALES SPECIFICATION 1

For more information and technical assistance contact:

Chevron Phillips Chemical Company LP
P.O. Box 4910
The Woodlands, TX 77387-4910
800.231.3260

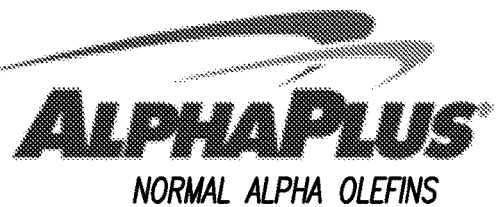

NORMAL ALPHA OLEFINS

AlphaPlus® 1-Dodecene
Sales Specifications

| Characteristics | Method | Units | Target | Minimum | Maximum | Note |
|---|---|---|---|---|---|---|
| Less than $C_{10}$ | GLC | Wt % | --- | --- | 0.05 | --- |
| $C_{10}$ | GLC | Wt % | --- | --- | 1.00 | --- |
| $C_{12}$ | GLC | Wt % | --- | 98.0 | --- | --- |
| $C_{14}$ | GLC | Wt % | --- | --- | 2.00 | --- |
| Greater than $C_{14}$ | GLC | Wt % | --- | --- | 0.05 | --- |
| n-Alpha Olefin | GLC | Wt % | --- | 94.6 | --- | --- |
| Vinylidene | GLC | Wt % | --- | --- | 4.2 | --- |
| cis-and trans-2-Dodecene | GLC | Wt % | --- | --- | 0.34 | --- |
| Paraffin | GLC | Wt % | --- | --- | 0.34 | --- |
| Water | ASTM E1064 | PPM by Wt | --- | --- | 100 | --- |
| Color | ASTM D6045 | Saybolt | --- | 30 | --- | --- |
| Appearance | ASTM D4176 | --- | --- | Clear and Bright | --- | --- |
| API Gravity @ 60°F | ASTM D4052 | --- | --- | --- | --- | note 1 |
| Specific Gravity @ 60°F/60°F | ASTM D4052 | --- | --- | --- | --- | note 1 |

1. Run and record

MSDS # 100000068203        Revision Date July 2010

Another quality product from Chevron Phillips Chemical Company LP The Woodlands, Texas Before using this product, the user is advised and cautioned to make its own determination and assessment of the safety and suitability of the product for the specific use in question and is further advised against relying on the information contained herein as it may relate to any specific use or application. It is the ultimate responsibility of the user to ensure that the product is suited and the information is applicable to the user's specific application. Chevron Phillips Chemical Company LP does not make, and expressly disclaims, all warranties, including warranties of merchantablity or fitness for a particular purpose, regardless of whether oral or written, express or implied, or allegedly arising from any usage of any trade or from any course of dealing in connection with the use of the information contained herein or the product itself. The user expressly assumes all risk and liability, whether based in contract, tort or otherwise, in connection with the use of the information contained herein or the product itself. Further, information contained herein is given without reference to any intellectual property issues, as well as federal, state or local laws which may be encountered in the use thereof. Such questions should be investigated by the user.

Page 1 of 1

FIG. 2

SALES SPECIFICATION 2

For more information and technical assistance contact:

Chevron Phillips Chemical Company LP
P.O. Box 4910
The Woodlands, TX 77387-4910
800.231.3260

NORMAL ALPHA OLEFINS

AlphaPlus® 1-Tetradecene
Sales Specifications

| Characteristics | Method | Units | Target | Minimum | Maximum | Note |
|---|---|---|---|---|---|---|
| Less than $C_{12}$ | GLC | Wt % | --- | --- | 0.05 | --- |
| $C_{12}$ | GLC | Wt % | --- | --- | 1.00 | --- |
| $C_{14}$ | GLC | Wt % | --- | 98.0 | --- | --- |
| $C_{16}$ | GLC | Wt % | --- | --- | 2.00 | --- |
| Greater than $C_{16}$ | GLC | Wt % | --- | --- | 0.05 | --- |
| n-Alpha Olefin | GLC | Wt % | --- | 93.4 | --- | --- |
| Vinylidene | GLC | Wt % | --- | --- | 5.4 | --- |
| cis-and trans-2-Tetradecene | GLC | Wt % | --- | --- | 0.34 | --- |
| Paraffin | GLC | Wt % | --- | --- | 0.34 | --- |
| Water | ASTM E1064 | PPM by Wt | --- | --- | 100 | --- |
| Color | ASTM D6045 | Saybolt | --- | 30 | --- | --- |
| Appearance | ASTM D4176 | --- | --- | Clear and Bright | --- | --- |
| API Gravity @ 60°F | ASTM D4052 | --- | --- | --- | --- | note 1 |
| Specific Gravity @ 60°F/60°F | ASTM D4052 | --- | --- | --- | --- | note 1 |

1. Run and record

MSDS # 100000067489

Revision Date July 2010

Another quality product from Chevron Phillips Chemical Company LP The Woodlands, Texas Before using this product, the user is advised and cautioned to make its own determination and assessment of the safety and suitability of the product for the specific use in question and is further advised against relying on the information contained herein as it may relate to any specific use or application. It is the ultimate responsibility of the user to ensure that the product is suited and the information is applicable to the user's specific application. Chevron Phillips Chemical Company LP does not make, and expressly disclaims, all warranties, including warranties of merchantablity or fitness for a particular purpose, regardless of whether oral or written, express or implied, or allegedly arising from any usage of any trade or from any course of dealing in connection with the use of the information contained herein or the product itself. The user expressly assumes all risk and liability, whether based in contract, tort or otherwise, in connection with the use of the information contained herein or the product itself. Further, information contained herein is given without reference to any intellectual property issues, as well as federal, state or local laws which may be encountered in the use thereof. Such questions should be investigated by the user.

Page 1 of 1

FIG. 3

SALES SPECIFICATION 3

Shell Chemicals
Technical Data Sheet

NEODENE® 12

Higher Olefins

Issued: November 2015
SICC Product Code: V1142

Description:

NEODENE® 12 Linear Alpha Olefin is high purity 1-dodecene made by the Shell Higher Olefins Process (SHOP) by the oligomerisation of ethylene.

| | Property | Unit | Value | Method |
|---|---|---|---|---|
| TYPICAL CHEMICAL PROPERTIES[a] | C10 and lower | %m/m | < 1 | SMS2895 |
| | C12 | %m/m | > 97 | SMS2895 |
| | C14 and higher | %m/m | < 2 | SMS2895 |
| | Total n-Alpha Olefins | %m/m | > 94.0 | SMS2895 |
| | Branched + Internal Olefins | %m/m | < 6.0 | SMS2895 |
| | Total Paraffins | %m/m | < 0.2 | SMS2895 |
| | Appearance | | CSFVI[b] | Visual |
| | Color, Pt-Co | Pt-Co | < 5 | ASTM D1209 |
| | Carbonyl as C=O | mg/kg | < 15 | SMS2894 |
| | Peroxides as O | mg/kg | < 3.0 | SMS359 |
| | Water | mg/kg | < 100 | ASTM E1064 | a: An official sales specification is available from your local Shell Chemicals representative.
b: Clear & Substantially free of visual impurities www.shell.com/chemicals Shell Global Solutions, One Shell Plaza, 910 Louisiana, Houston, TX 77002-4916, United States of America

FIG. 4A

Technical Data Sheet

| | Property | Unit | Value |
|---|---|---|---|
| Typical Physical Properties[a] | Density @ 20°C | kg/l | 0.762 |
| | Boiling Point Range | °C | 200–252 |
| | Flashpoint | °C | 83 |
| | Freezing point | °C | −36 |
| | Kinematic viscosity @ 20°C | mm2/s | 1.8 | a: An official sales specification is available from your local Shell Chemicals representative.

Storage and Handling

NEODENE® Alpha Olefins can be supplied with or without antioxidant as requested. Advice on the storage and handling of NEODENE® Linear Alpha Olefins can be found in the Safety Data Sheet on our website at www.shell.com/chemicals/msds or by contacting your local Shell Chemicals Representative.

Hazard Identification

Alpha Olefins are potentially hazardous material; everyone concerned with handling it must be conversant with the nature of the hazards and trained in the recommended handling procedures for both normal and emergency situations. Before handling the product refer to the Safety Data Sheet that is available on our website at www.shell.com/chemicals/msds or by contacting your local Shell Chemicals Representative.

Emergency Helpline

For emergency telephone numbers refer to the Safety Data Sheet relevant for your company's country and language.

Shell Warranties

NEODENE® is a Shell trademark.

The expression 'Shell Chemicals' refers to the companies of Royal Dutch/Shell Group which are engaged in chemical businesses. Each of the companies which make up the Royal Dutch/Shell Group of companies is an independent entity and has its own separate identity.

The information contained in this publication is to the best of our knowledge, true and accurate, but any recommendations or suggestions that may be made are without guarantee, since the conditions of use are beyond our control. Furthermore, nothing contained herein shall be construed as a recommendation to use any product in conflict with existing patents covering any material or its use.

NEODENE®12                www.shell.com/chemicals          Page 2

Shell Chemicals, One Shell Plaza, 910 Louisiana, Houston, TX 77002-4916, United States of America

FIG. 4B

INEOS Oligomers   SALES SPECIFICATION 4

*Alpha Olefin C12 (dodecene-1)*
*Sales Specifications*

| Property | Units | Method | Min | Max | Comments |
|---|---|---|---|---|---|
| Carbon Number C10 & lighter | wt% | AAM 5466 | -- | 2 | |
| Carbon Number C12 | wt% | AAM 5466 | 97 | -- | |
| Carbon Number C14 & heavier | wt% | AAM 5466 | -- | 2 | |
| Hydrocarbon Type, Mono-olefin | wt% | AAM 5469 | 99 | -- | 100 minus percent paraffins |
| Hydrocarbon Type, Paraffin | wt% | AAM 5469 | -- | 1 | |
| Olefin Isomers, Linear Terminal | mol% | AAM 5484 | 89 | -- | |
| Olefin Isomers, Branched Terminal | mol% | AAM 5484 | -- | 10 | |
| Olefin Isomers, Linear Internal | mol% | AAM 5484 | -- | 4 | |

Technical information contained herein is furnished without charge or obligation, and is given and accepted at recipient's sole risk. Because conditions of use may vary and are beyond our control, INEOS makes no representation about, and is not responsible or liable for the accuracy or reliability of data, nor for toxicological effects or Industrial Hygiene requirements associated with particular uses of any product described herein. Nothing contained in this document shall be considered a recommendation for any use that may infringe patent rights, or an endorsement of any particular material, equipment, service, or other item not supplied by INEOS. The "Properties" and "Applications" listed in this document are not specifications. They are provided as information only and in no way modify, amend, enlarge, or create any specification or warranty, and ALL WARRANTIES, EXPRESS OR IMPLIED, INCLUDING WITHOUT LIMITATION THE WARRANTIES OF MERCHANTABILITY AND FITNESS FOR A PARTICULAR PURPOSE, ARE EXCLUDED.

The name INEOS is a trademark of INEOS Capital Limited.

FIG. 5

SALES SPECIFICATION 5

Shell Chemicals
Technical Data Sheet

NEODENE® 14

Higher Olefins

Issued: November 2015
SICC Product Code: V1143

Description:

NEODENE® 14 Linear Alpha Olefin is high purity 1-tetradecene made by the Shell Higher Olefins Process (SHOP) by the oligomerisation of ethylene.

| | Property | Unit | Value | Method |
|---|---|---|---|---|
| TYPICAL CHEMICAL PROPERTIES[a] | C12 and lower | %m/m | <2 | SMS2895 |
| | C14 | %m/m | > 95 | SMS2895 |
| | C16 and higher | %m/m | < 3 | SMS2895 |
| | Total n-Alpha Olefins | %m/m | > 93 | SMS2895 |
| | Branched + Internal Olefins | %m/m | < 7.0 | SMS2895 |
| | Total Paraffins | %m/m | < 0.2 | SMS2895 |
| | Appearance | | CSFVI[b] | Visual |
| | Color, Pt-Co | | <5 | ASTM D1209 |
| | Carbonyl as C=O | mg/kg | <15 | SMS2894 |
| | Peroxides as O | mg/kg | <3 | SMS359 |
| | Water | mg/kg | <100 | ASTM E1064 | a: An official sales specification is available from your local Shell Chemicals representative.
b: Clear & Substantially free of visual impurities www.shell.com/chemicals Shell Global Solutions, One Shell Plaza, 910 Louisiana, Houston, TX 77002-4916, United States of America

FIG. 6A

Technical Data Sheet

| | Property | Unit | Value |
|---|---|---|---|
| Typical Physical Properties | Density @ 20°C | kg/l | 0.771 |
| | Boiling Point Range | °C | 214-285 |
| | Flashpoint | °C | 113 |
| | Freezing point | °C | -13 |
| | Kinematic viscosity @ 20°C | mm2/s | 2.7 |

Storage and Handling

NEODENE® Alpha Olefins can be supplied containing antioxidant as requested. Advice on the storage and handling of NEODENE® Linear Alpha Olefins can be found in the Safety Data Sheet on our website at www.shell.com/chemicals/msds or by contacting your local Shell Chemicals Representative.

Hazard Identification

Alpha Olefins are potentially hazardous material; everyone concerned with handling it must be conversant with the nature of the hazards and trained in the recommended handling procedures for both normal and emergency situations. Before handling the product refer to the Safety Data Sheet that is available on our website at www.shell.com/chemicals/msds or by contacting your local Shell Chemicals Representative.

Emergency Helpline

For emergency telephone numbers refer to the Safety Data Sheet relevant for your company's country and language.

Shell Warranties

NEODENE® is a Shell trademark.

The expression 'Shell Chemicals' refers to the companies of Royal Dutch/Shell Group which are engaged in chemical businesses. Each of the companies which make up the Royal Dutch/Shell Group of companies is an independent entity and has its own separate identity.

The information contained in this publication is to the best of our knowledge, true and accurate, but any recommendations or suggestions that may be made are without guarantee, since the conditions of use are beyond our control. Furthermore, nothing contained herein shall be construed as a recommendation to use any product in conflict with existing patents covering any material or its use.

NEODENE®14    www.shell.com/chemicals    Page 2

Shell Chemicals, One Shell Plaza, 910 Louisiana, Houston, TX 77002-4916, United States of America

FIG. 6B

INEOS Oligomers

SALES SPECIFICATION 6

*Alpha Olefin C14 (tetradecene-1)*
*Sales Specifications*

| Property | Units | Method | Min | Max | Comments |
|---|---|---|---|---|---|
| Carbon Number C12 | wt% | AAM 5466 | -- | 3 | |
| Carbon Number C14 | wt% | AAM 5466 | 95 | -- | |
| Carbon Number C16 | wt% | AAM 5466 | -- | 3 | |
| Hydrocarbon Type, Mono-olefin | wt% | AAM 5469 | 99 | -- | 100 minus percent paraffins |
| Hydrocarbon Type, Paraffin | wt% | AAM 5469 | -- | 1 | |
| Olefin Isomers, Linear Terminal | mol% | AAM 5484 | 75 | -- | |

Technical information contained herein is furnished without charge or obligation, and is given and accepted at recipient's sole risk. Because conditions of use may vary and are beyond our control, INEOS makes no representation about, and is not responsible or liable for the accuracy or reliability of data, nor for toxicological effects or Industrial Hygiene requirements associated with particular uses of any product described herein. Nothing contained in this document shall be considered a recommendation for any use that may infringe patent rights, or an endorsement of any particular material, equipment, service, or other item not supplied by INEOS. The "Properties" and "Applications" listed in this document are not specifications. They are provided as information only and in no way modify, amend, enlarge, or create any specification or warranty, and ALL WARRANTIES, EXPRESS OR IMPLIED, INCLUDING WITHOUT LIMITATION THE WARRANTIES OF MERCHANTABILITY AND FITNESS FOR A PARTICULAR PURPOSE, ARE EXCLUDED.

The name INEOS is a trademark of INEOS Capital Limited.

FIG. 7

ALCOHOLS PRODUCTION

CROSS-REFERENCE TO RELATED APPLICATIONS

This patent application is a US nonprovisional patent application of and claims benefit of the filing date of copending U.S. provisional patent application No. 63/035,073 titled "Alcohols Production" filed Jun. 5, 2020 (5 Jun. 2020).

FIELD OF THE INVENTION

The present invention relates to branched alcohols and methods for producing and manufacturing branched alcohols.

INCORPORATION BY REFERENCE

This patent application incorporates by reference in its entirety copending U.S. provisional patent application No. 63/035,073 titled "Alcohols Production" filed Jun. 5, 2020 (5 Jun. 2020).

BACKGROUND OF THE INVENTION

The chemical industry has suffered a long felt need to produce branched alcohols in a cost-effective manner. There is a ready and large supply of alpha olefins which are inexpensive. However, there is no known way to efficiently and cost effectively produce branched alcohols on an industrial scale using alpha olefins as a feedstock.

SUMMARY OF THE INVENTION

In an embodiment, a process can have the steps of: providing CO and H2; providing a first catalyst which is an organometallic complex of rhodium and one type of an organophosphorus ligand or an organometallic complex of rhodium and more than one type of an organophosphorus ligand; providing a linear alpha olefin; isomerizing the linear alpha olefin (also herein described as a normal alpha olefin) by the first catalyst in the presence of CO and H2 at a first pressure to produce an isomerized olefin; and hydroformylating the isomerized olefin by the first catalyst in the presence of CO and H2 at a second pressure different from the first pressure to produce a branched aldehyde. In an embodiment, the branched aldehyde is a 2-alkyl branched aldehyde. In an embodiment, the linear alpha olefin is a C4-C36 linear alpha olefin. In an embodiment, the branched aldehyde produced from the C4-C36 linear alpha olefin is a C5-C37 branched aldehyde. In an embodiment, the linear alpha olefin can be 1-Butene and the branched aldehyde can be branched Pentanals. In an embodiment, the linear alpha olefin can be 1-Hexene and the branched aldehyde can be branched Heptanals. In an embodiment, the linear alpha olefin can be 1-Octene and the branched aldehyde can be branched Nonanals. In an embodiment, the linear alpha olefin can be 1-Decene and the branched aldehyde can be branched Undecanals. In an embodiment, the linear alpha olefin can be 1-Dodecene and the branched aldehyde can be branched Tridecanals. In an embodiment, the linear alpha olefin can be 1-Tetradecene and the branched aldehyde can be branched Pentadecanals.

In an embodiment, the linear alpha olefin can be 1-Hexadecene and the branched aldehyde can be branched Heptadecanals. In an embodiment, the linear alpha olefin can be 1-Octadecene and the branched aldehyde can be branched Nonadecanals. In an embodiment, the organophosphorous ligand can be a phosphine. In a nonlimiting example of a phosphine ligand, the phosphine ligand can be triphenylphosphine. In another embodiment, the organophosphorous ligand can be a phosphite. In a nonlimiting example of a phosphite ligand, the phosphite ligand can be tris (2,4-di-t-butylphenyl) phosphite. In yet another embodiment, a mixture of organophosphorous ligands of different types can be used, such as a mixture of a phosphine and a phosphite. In a nonlimiting example of a mixture of organophosphorous ligands, the organophosphorous ligands can be a mixture of triphenylphosphine and tris (2,4-di-t-butylphenyl) phosphite.

In an embodiment, the first catalyst is formed when the molar ratio of phosphorous to rhodium is in a range of 1:1 to 1000:1. In an embodiment, the first catalyst is formed when the molar ratio of phosphorous to rhodium is in a range of 1:1 to 1000:1 in the isomerization step and/or reactor. In an embodiment, the first catalyst is formed when the molar ratio of phosphorous to rhodium is in a range of 1:1 to 1000:1 in the hydroformylation step and/or reactor.

BRIEF DESCRIPTION OF THE DRAWINGS

The present invention in its several aspects and embodiments solves the problems discussed above and significantly advances the technology of branched compounds and methods for producing and manufacturing branched compounds. The present invention can become more fully understood from the detailed description and the accompanying drawings, wherein:

FIG. 2 shows Sales Specification 1;
FIG. 3 shows Sales Specification 2;
FIG. 4A shows Sales Specification 3, page 1;
FIG. 4B shows. Sales Specification 3, page 2;
FIG. 5 shows Sales Specification 4;
FIG. 6A shows Sales Specification 5, page 1;
FIG. 6B shows Sales Specification 5, page 2;
and
FIG. 7 shows Sales Specification 6.

Herein, like reference numbers in one figure refer to like reference numbers in another figure.

DETAILED DESCRIPTION OF THE INVENTION

Figure 1:
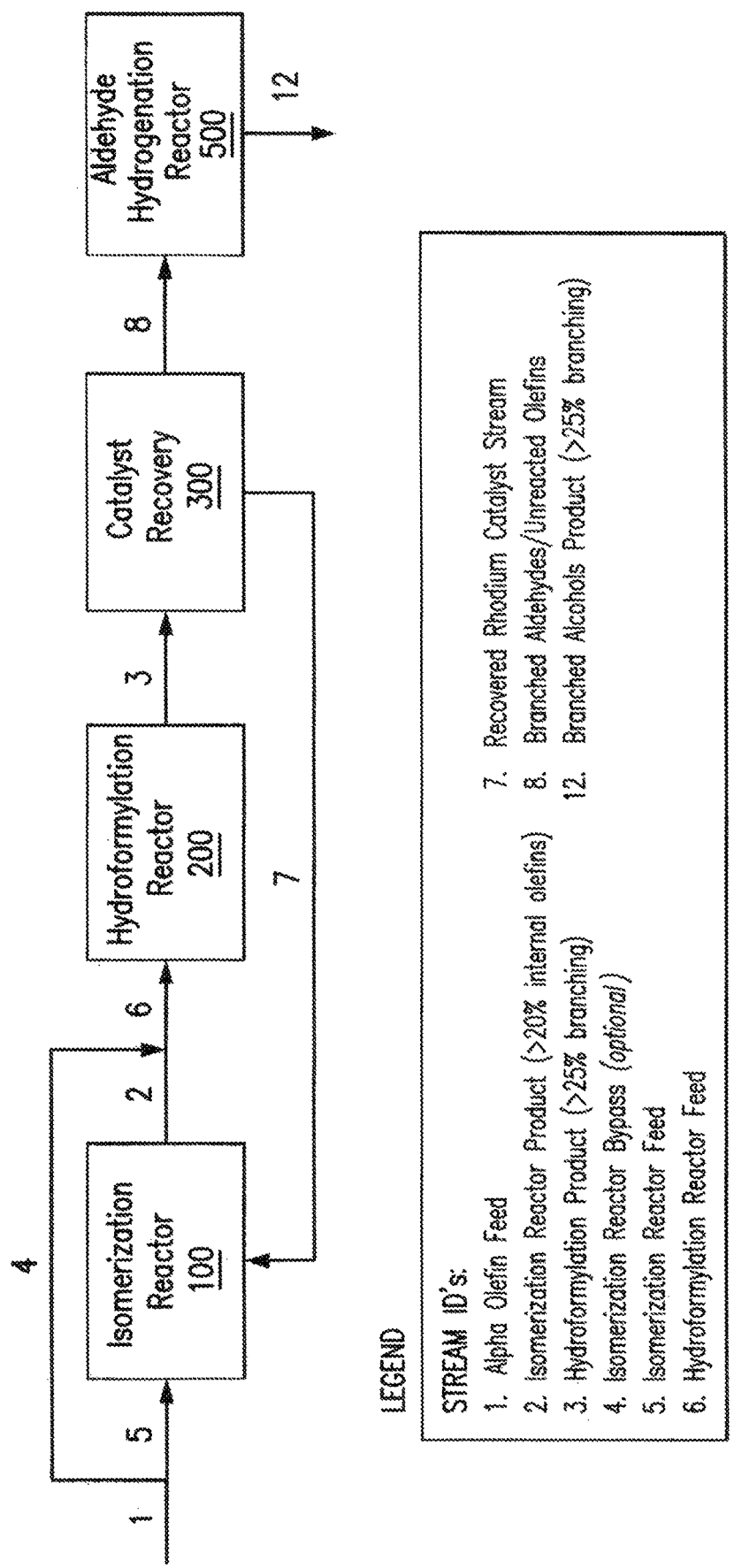
FIG. 1 shows an embodiment of a chemical manufacturing process having an isomerization reactor, a hydroformylation reactor, catalyst recovery and an aldehyde hydrogenation reactor.

Described herein is a process for the production of branched C13 and C15 aldehydes and alcohols. According to a nonlimiting embodiment of this process, e.g. as shown in FIG. 1, branched C13 aldehydes (branched Tridecanals) and branched C13 alcohols (branched Tridecanols) can be produced from a C12 linear alpha olefin (i. e. 1-Dodecene). Examples of sales specifications for commercially available C12 linear alpha olefins are shown in. FIG. 2, FIG. 4A/4B, and FIG. 5. In another embodiment of this process, branched C15 aldehydes (branched Pentadecanals) and branched C15 alcohols (branched Pentadecanols) can be produced from a C14 linear alpha olefin (i.e. 1-Tetradecene). Examples of sales specifications for commercially available C14 linear alpha olefins are shown in FIG. 3, FIG. 6A/6B, and FIG. 7.

A two-step process is disclosed herein which produces highly branched aldehyde products from linear alpha olefin feedstocks. The two-step process uses a rhodium organophosphorus catalyst for both the first process step and the second step. The first step is an isomerization reaction step and the second process step is a hydroformylation reaction step. The highly branched aldehydes can undergo a further hydrogenation step to produce highly branched alcohols.

Numeric values and ranges herein, unless otherwise stated, also are intended to have associated with them a tolerance and to account for variances of design and manufacturing. Thus, a number can include values "about" that number. For example, a value X is also intended to be understood as "about X". Likewise, a range of Y-Z, is also intended to be understood as within a range of from "about Y-about Z". Unless otherwise stated, significant digits disclosed for a number are not intended to make the number an exact limiting value. Variance and tolerance are inherent in mechanical design and the numbers disclosed herein are intended to be construed to allow for such factors (in non-limiting e.g., ±10 percent of a given value). Likewise, the claims are to be broadly construed in their recitations of numbers and ranges.

Every numerical range given throughout this specification will include every narrower numerical range that falls within such broader numerical range, as if such narrower numerical ranges were all expressly written herein. As regarding ranges and endpoints, every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein.

Unless otherwise stated temperatures recited herein are in degrees Celsius ("° C.").

Unless otherwise stated pressures recited herein are in bar(g), i.e. bars gauge. Herein, 0 bar(g) is atmospheric pressure, e.g. 14.70 psia (aka 0 psig).

Unless otherwise stated percentages of composition recited herein are on a weight basis and disclosed as weight percent (wt. %).

Alternatively, herein, concentration can be expressed in units of parts per million, or ppm.

Herein "branched" is defined as a molecule, compound or chemical structure, having one or more alkyl groups attached along a carbon backbone. "Branched" molecules are isomers of linear (i.e. straight-chain) molecules having the same number of carbon atoms.

Herein, the term "percent branched", in additional to its ordinary and customary meaning, is defined herein to mean the wt. % branched molecules in a composition. The term "percent branching" is use synonymously with "percent branched" and has the same meaning as "percent branched". As an example, for an aldehyde composition, the "percent branching" of the aldehyde means the wt. % of the aldehyde being branched, i.e.:

Percent branching %=percent branched %=100*(wt. % branched aldehyde)÷(wt. branched aldehyde+ wt. % linear aldehyde).

As an example, a branched C6 aldehyde composition comprising:

| 25 wt. % 1-Hexanal | (linear molecule) |
|---|---|
| 40 wt. % 2-Methyl-Pentanal | (branched molecule) |
| 35 wt. % 2-Ethyl-butanal | (branched molecule) |
| would have a Percent Branching = 75% | |

Unless otherwise stated percent branching recited herein are in weight percent (wt. %) is calculated based upon reactant and product weights, excluding nonparticipating compounds.

Herein, the term "percent isomerized", in additional to its ordinary and customary meaning, is defined herein to mean the wt. % of olefin molecules where the olefin has been isomerized from the alpha position to an internal olefin position. Specifically, the "percent isomerized" means the wt. % of the olefin composition being internal olefins, i.e.:

Percent isomerized %=100*(wt. % internal olefin)÷(wt. % alpha olefin+wt. % internal olefin).

As an example, a C12 alpha olefin isomerized to produce a composition comprising:

| 25 wt. % 1-Dodecene | (alpha olefin) |
|---|---|
| 40 wt. % 2-Dodecene | (internal olefin)) |
| 35 wt. % 3-Dodecene | (internal olefin) |
| would have a Percent Isomerized = 75% | |

Unless otherwise stated the term "internal olefin" recited herein means an olefin in which a double bond is present in a position other than the alpha position.

Unless otherwise stated percent isomerized recited herein are in weight percent (wt. %) is calculated based upon reactant and product weights, excluding nonparticipating compounds.

FIG. 1 shows an embodiment of a chemical manufacturing process having an isomerization reactor, a hydroformylation reactor, catalyst recovery and an aldehyde hydrogenation reactor.

FIG. 1 shows an embodiment in which Stream 8 is fed to an aldehyde hydrogenation reactor 500 which produces branched alcohols as Stream 12 which is a branched alcohols product stream.

FIG. 1 shows an embodiment in which Stream 8 is the feed stream to the Aldehyde Hydrogenation Reactor (500) and can have a composition, e.g.:

1. A C5-C37 aldehyde mixture containing,
   a. >25 wt. % branched aldehydes,
   b. <75 wt. % linear aldehydes, and
2. Unreacted C4-C36 olefins.

In the embodiment of FIG. 1, the C5-C37 aldehydes are hydrogenated in the Aldehyde Hydrogenation Reactor (500) in the presence of hydrogen and a hydrogenation catalyst, e.g. Catalyst A, to produce Stream 12. Stream 12 is a branched alcohols product and in an embodiment can have a composition comprising:

1. A C5-C37 alcohol mixture containing,
   a. >30 wt. % branched alcohols,
   b. <70 wt. % linear alcohols, and
2. C4-C36 paraffins (alkanes).

In the embodiment of FIG. 1, the C5-C37 alcohols are produced from the hydrogenation of the corresponding aldehydes in aldehyde hydrogenation reactor 500 and the C4-C36 paraffins also produced in aldehyde hydrogenation reactor 500 resulting from the hydrogenation of the unreacted C4-C36 olefins contained in Stream 8.

Optionally, the C5-C37 alcohols content (purity) can be increased in Stream 12, with a related decrease in the C4-C36 paraffin content by using an optional distillation step after aldehyde hydrogenation reactor 500 to remove, the low-boiling C4-C36 paraffins and produce a distilled, high purity C5-C37 Branched Alcohols Product which is free of, or nearly free of, C4-C36 paraffins.

Stream 1—Alpha Olefin Feed Composition.
Stream 2—Isomerization Reactor Product Composition.
Stream 3—Hydroformylation Product Composition.
Stream 4—Isomerization Reactor Bypass Composition.
Stream 5—Isomerization Reactor Feed Composition.
Stream 6—Hydroformylation Reactor Feed Composition.
Stream 7—Recovered Rhodium Catalyst Stream Composition.
Stream 8—Branched Aldehydes/Unreacted Olefins Composition.
Stream 12, Branched Alcohols Product.

In an embodiment, Stream 12 can be a branched alcohols product composition having greater than 40% branching.

In the embodiment of FIG. 1, the starting Alpha Olefin Feed Composition is shown as Stream 1. In this embodiment, Stream 1 can be split into Stream 5 (Isomerization Reactor Feed Composition) which is fed to Isomerization Reactor 100 and Stream 4 (Isomerization Reactor Bypass Composition) which can be bypassed around Isomerization Reactor 100 and be provided as a feed to the Hydroformylation reaction. The use of a bypass stream, e.g. Stream 4, is optional. It is not necessary to bypass of a portion of the alpha olefin feed around Isomerization Reactor 100; however, using a bypass such as Stream 4 can provide a means to control the percentage of alpha olefin isomerization achieved in Stream 6, the feed stream to Hydroformylation Reactor 200.

In the embodiment of FIG. 1, the effluent of Isomerization Reactor 100, i.e. Stream 2—Isomerization Reactor Product Composition, is combined with Stream 4—Isomerization Reactor Bypass Composition to produce Stream 6—Hydroformylation Reactor Feed Composition which is fed to Hydroformylation Reactor 200.

In the embodiment of FIG. 1, Hydroformylation Reactor 200 produces Stream 3—Hydroformylation Product Composition.

In the embodiment of FIG. 1, the Stream 3—Hydroformylation Product Composition is fed to Catalyst Recovery 300 which produces Stream 7—Recovered Rhodium Catalyst Stream Composition as recycle feed to Isomerization Reactor 100 and Stream 8—Branched Aldehydes/Unreacted Olefins Composition. In FIG. 1 catalyst recovery is shown as occurring in the unit operation shown as Catalyst Recovery 300.

In the embodiment of FIG. 1, Stream 8—Branched Aldehydes/Unreacted Olefins Composition is fed to Aldehyde Hydrogenation Reactor 500 which produces Stream 12, Branched Alcohols Product.

Catalyst Specifications & Composition

The isomerization and hydroformylation reactions disclosed herein can be catalyzed by a rhodium organophosphorus catalyst which can be at least one of: (1) an organometallic complex of rhodium and one type of an, organophosphorus ligand; (2) or an organometallic complex of rhodium and more than one type of an organophosphorus ligand.

In an embodiment, the organophosphorous ligand can be a phosphine. In a nonlimiting example of a phosphine ligand, the phosphine ligand can be triphenylphosphine. In another embodiment, the organophosphorous ligand can be a phosphite. In a nonlimiting example of a phosphite ligand, the phosphite ligand can be tris (2,4-di-t-butylphenyl) phosphite. In yet another embodiment, a mixture of organophosphorous ligands of different types can be used, such as a mixture of a phosphine and a phosphite. In a nonlimiting example of a mixture of organophosphorous ligands, the organophosphorous ligands can be a mixture of triphenylphosphine and tris (2,4-di-t-butylphenyl) phosphite. In an embodiment, the reaction system can contain an inert high-boiling solvent, for example a polyalphaolefin. In an embodiment, the first catalyst can be formed when the molar ratio of phosphorous to rhodium is in a range of 1:1 to 1000:1, or 5:1 to 50:1, or 15:1 to 25:1. In an embodiment, the rhodium concentration can be in a range of 1 ppm to 1000 ppm, or 10 ppm to 200 ppm, or 25 ppm to 75 ppm. In an embodiment, the CO to H2 molar ratio can be in a range of 10:1 to 1:10, or 2:1 to 1:2, or 1.3:1 to 1:1.3.

Isomerization

In an embodiment, the first process step can be a reaction isomerizing a linear alpha olefin in the presence of Carbon Monoxide (CO) and Hydrogen (H2) at a first pressure. The isomerizing can be catalyzed by the rhodium organophosphorus catalyst which can be at least one of: (1) an organometallic complex of rhodium and one type of an organophosphorus ligand; (2) or an organometallic complex of rhodium and more than one type of an organophosphorus ligand. The isomerization reactions can produce an isomerized olefin comprising linear internal olefins of the same or different types.

In an embodiment, the isomerization step can be performed at a temperature in a range of 30° C. to 500° C., or 50° C. to 150° C., or 70° C. to 100° C. In an embodiment, the isomerization step can be performed at a pressure in a range of 0.1 bar(g) to 10 bar(g), or 0.5 bar(g) to 5 bar(g), or 1 bar(g) to 2 bar(g).

In an embodiment, the isomerizing step can produce a reaction product comprising a 20 wt. % or greater isomerized olefin, or a 40 wt. % or greater isomerized olefin, or a 60 wt. % or greater isomerized olefin, or a 90 wt. % or greater isomerized olefin.

In the embodiment of FIG. 1, the isomerizing step is shown as occurring in Isomerization Reactor 100.

Hydroformylation

The second process step of this embodiment can be a reaction hydroformylating the isomerized olefin in the presence of CO and H2 at a second pressure higher than the first pressure to produce a branched aldehyde. The hydroformylation reaction can be catalyzed by the rhodium organophosphorus catalyst which can be at least one of: (1) an organometallic complex of rhodium and one type of an organophosphorus ligand; (2) or an organometallic complex of rhodium and more than one type of an organophosphorus ligand. In an embodiment, the branched aldehyde is a 2-alkyl branched aldehyde. In an embodiment, the linear alpha olefin can be 1-Dodecene and the branched aldehyde can be a branched C13 aldehyde. In an embodiment, the linear alpha olefin can be 1-Tetradecene and the branched aldehyde can be a branched C15 aldehyde.

In an embodiment, the hydroformylating step can be performed at a temperature in a range of 30° C. to 500° C., or 50° C. to 150° C., or 70° C. to 100° C. In an embodiment, the hydroformylating step can be performed at a pressure in a range of 5 bar(g) to 400 bar(g), or 10 bar(g) to 100 bar(g), or 15 bar(g) to 20 bar(g).

In an embodiment, the hydroformylating step can produce a reaction product comprising a 25 wt % or greater branched aldehyde, or a 40 wt. % or greater branched aldehyde, or a 60 wt. % or greater branched aldehyde, or a 90 wt. % or greater branched aldehyde.

In the embodiment of FIG. 1, the hydroformylating steps is shown as occurring in Hydroformylation Reactor 200.

Hydroformylation Product Distillation

In an embodiment, the products of the hydroformylation reaction can be distilled. In this embodiment, the process can have the step of separating the branched aldehyde products resulting from hydroformylation as an overhead product from the first catalyst stream via a distillation process. The distillation step can be performed at a temperature in a range of 100° C. to 200° C., or 125° C. to 175° C. The distillation step can be performed under vacuum at a pressure of less than 500 millibar absolute, or less than 100 millibar absolute, or less than 30 millibar absolute.

Hydrogenation

In an embodiment, this process can also have the steps of: hydrogenating the branched aldehyde product in the presence of a hydrogenation catalyst to produce a branched alcohols product composition. In an embodiment, the hydrogenating catalyst can be a base metal catalyst, a supported nickel catalyst, a supported cobalt catalyst, a Raney® (W. R. Grace & Co., 7500 Grace Drive, Columbia, Md. 21044, US, phone 1-410-531-4000) nickel catalyst or a precious metal catalyst. In an embodiment, the hydrogenating step can be performed at a temperature in a range of 30° C. to 500° C., or 50° C. to 200° C., or 100° C. to 150° C. In an embodiment, the hydrogenating step can be performed at a pressure in a range of 5 bar(g) to 400 bar(g), or 10 bar(g) to 100 bar(g), or 30 bar(g) to 50 bar(g).

In the embodiment of FIG. 1, the step of hydrogenating the branched aldehyde product in the presence of a hydrogenation catalyst to produce a branched alcohols product composition is shown as occurring in Aldehyde Hydrogenation Reactor 500.

In an embodiment, the hydrogenating step can produce a reaction, product comprising 25 wt. % or greater branched alcohols, or 40 wt. % or greater branched alcohols, or 60 wt. % or greater branched alcohols, or 90 wt. % or greater branched alcohols.

EXAMPLE 1: PREPARATION OF A BRANCHED C13 ALCOHOL PRODUCT

A C12 linear alpha olefin feedstock (1-Dodecene) was obtained from the Chevron Phillips Chemical Company. LP, as identified by product name AlphaPlus® 1-Dodecene (Chevron Phillips Chemical Company LP, P.O. Box 4910, The Woodlands, Tex. 77387-4910, US, phone (800) 231-3260). The homogeneous rhodium organophosphorus catalyst used in this example is prepared in a high pressure, stainless steel stirred autoclave. To the autoclave was added 0.027 wt. % Rh(CO)2ACAC ((Acetylacetonato)dicarbonylrhodium(I)), 1.36 wt. % tris (2,4,-di-t-butylphenyl) phosphite ligand and 98.62 wt. % Synfluid® PAO 4 cSt (Chevron Phillips Chemical Company LP, P.O. Box 4910, The Woodlands, Tex. 77387-4910, phone (800) 231-3260) inert solvent. The mixture was heated at 80° C. in the presence of a CO/H2 atmosphere and 2 bar(g) pressure for four hours to produce the active rhodium catalyst solution (109 ppm rhodium, P:Rh molar ratio=20). The 1-Dodecene linear alpha olefin was added to the rhodium catalyst solution in the autoclave producing a starting reaction mixture with a rhodium concentration of 35 ppm. The alpha olefin feed was then isomerized at 80° C. in the presence of a CO/H2 atmosphere and 1 bar(g) pressure for 10 hours. The isomerized olefin was then hydroformylated at 70° C. in the presence of a CO/H2 atmosphere and 20 bar(g) pressure for 8 hours. The molar ratio of CO to H2 in both the isomerization step and the hydroformylation step was equal to 1:1.15. The resulting hydroformylation reaction product was flash distilled at 140-150° C. and 25 millibar to recover the rhodium catalyst solution as a bottoms product and recover a branched C13 Aldehyde overheads product with a composition comprising:

|                  | Weight %  |
|------------------|-----------|
| 1-Tridecanal     | 13.9%     |
| 2-Methyl-dodecanal | 28.3%   |
| 2-Ethyl-undecanal | 15.2%    |
| 2-Propyl-decanal | 14.5%     |
| 2-Butyl-nonanal  | 13.6%     |
| 2-Pentyl-octanal | 12.6%     |
| TOTAL            | 98.0%     |

The weight % branching in the branched C13 aldehyde product was 86.2%.

The branched C13 aldehyde product was hydrogenated in a high pressure, Inconel 625 stirred autoclave at 150 C and 20 bar(g) hydrogen pressure. The hydrogenation catalyst used was a Raney® Nickel 3111 (W. R. Grace & Co., 7500 Grace Drive, Columbia, Md. 21044, US, phone 1-410-531-4000) catalyst used at a 0.25 wt. % loading. The aldehyde was hydrogenated for 10 hours and the resultant reaction mixture was filtered to produce a branched C13 alcohol product comprising:

|                    | Weight % |
|--------------------|----------|
| 1-Tridecanol       | 13.2%    |
| 2-Methyl-dodecanol | 29.1%    |
| 2-Ethyl-undecanol  | 15.5%    |
| 2-Propyl-decanol   | 14.4%    |
| 2-Butyl-nonanol    | 13.2%    |
| 2-Pentyl-octanol   | 12.9%    |
| TOTAL              | 98.4%    |

The weight % branching in the branched C13 alcohol product was 86.6%.

EXAMPLE 2: PREPARATION OF A BRANCHED C15 ALCOHOL PRODUCT

The recovered rhodium catalyst stream from Example 1 was charged to a high pressure, stainless steel stirred autoclave and a C14 linear alpha olefin feedstock (1-Tetradecene) from the Chevron Phillips Chemical Company LP, (AlphaPlus® 1-Tetradecene by Chevron Phillips Chemical Company LP, P.O. Box 4910, The Woodlands, Tex. 77387-4910, phone (800) 231-3260) was added. The resulting mixture had a rhodium concentration of approximately 30 ppm. The 1-tetradecene linear alpha olefin was then isomerized at 80° C. in the presence of a CO/H2 atmosphere and 1 bar(g) pressure for 12 hours. The isomerized olefin was then hydroformylated at 70° C. in the presence of a CO/H2 atmosphere and 20 bar(g) pressure for 8 hours. The resulting reaction product was flash distilled at 150-160° C. and 25 millibar to recover the rhodium catalyst solution as a bottoms product and recover a branched C15 Aldehyde overheads product. The recovered rhodium catalyst solution was then used again to complete a second 1-tetradecene batch isomerization (4 hours) and hydroformylation (6 hours). The resulting C15 aldehyde products from the two batches were combined to give a branched C15 Aldehyde product comprising:

|  | Weight % |
| --- | --- |
| 1-Pentadecanal | 12.1% |
| 2-Methyl-tetradecanal | 34.1% |
| 2-Ethyl-tridecanal | 21.9% |
| 2-Propyl-dodecanal | 14.0% |
| 2-Butyl-undecanal | 8.6% |
| 2-Pentyl-decanal | 9.0%* |
| TOTAL | 99.6% |

*This value includes the wt. % of 2-hexyl-nonanal.

The weight % branching in the branched C15 aldehyde product was 87.8%.

The branched C15 aldehyde product was hydrogenated in a high pressure, Inconel 625 stirred autoclave at 150C and 20 bar(g) hydrogen pressure. The hydrogenation catalyst used was a Raney® Nickel 3111 (W. R. Grace & Co., 7500 Grace Drive, Columbia, Md. 21044, US, phone 1-410-531-4000) catalyst used at a 0.25 wt. % loading. The aldehyde was hydrogenated for 10 hours and the resultant reaction mixture was filtered to produce a branched C15 alcohol product comprising:

|  | Weight % |
| --- | --- |
| 1-Pentadecanol | 13.7% |
| 2-Methyl-tetradecanol | 33.8% |
| 2-Ethyl-tridecanol | 21.4% |
| 2-Propyl-dodecanol | 12.4% |
| 2-Butyl-undecanol | 8.0% |
| 2-Pentyl-decanol | 9.2%* |
| TOTAL | 98.4% |

*This value includes the wt. % of 2-hexyl-nonanol.

The weight % branching in the branched C15 aldehyde product was 87.8%.
The weight % branching in the branched C15 alcohols product was 86.1%.

Conclusion

This disclosure regards branched compounds and methods for producing and manufacturing branched compounds in their many aspects, features and elements. Such compounds and manufacturing processes can be dynamic in use and operation. This disclosure is intended to encompass the equivalents, means, systems and methods of the use of the branched compounds and methods for producing and manufacturing branched compounds and their many aspects consistent with the description and spirit of the apparatus, means, methods, functions and operations disclosed herein. Other embodiments and modifications will be recognized by one of ordinary skill in the art as being enabled by and within the scope of this disclosure.

The scope of this disclosure is to be broadly construed. The embodiments herein can be used together, separately, mixed or combined. It is intended that this disclosure disclose equivalents, means, systems and methods to achieve the devices, designs, operations, control systems, controls, activities, mechanical actions, dynamics and results disclosed herein. For each compound, process, method, manufacturing method, mechanical element or mechanism disclosed, it is intended that this disclosure also encompasses within the scope of its disclosure and teaches equivalents, means, systems and methods for practicing the many aspects, compounds, processes, mechanisms and devices disclosed herein. The claims of this application are likewise to be broadly construed.

The description of the technology herein in its many and varied embodiments is merely exemplary in nature and, thus, variations that do not depart from the gist of the disclosure are intended to be within the scope of the claims and the disclosure herein. Such variations are not to be regarded as a departure from the spirit and scope of the disclosed technologies.

It will be appreciated that various modifications and changes can be made to the above-described embodiments of the processes and resulting chemical products as disclosed herein without departing from the spirit and the scope of the claims.

We claim:

1. A process, comprising the steps of:
providing CO and H2;
providing a first catalyst which is an organometallic complex of rhodium and one type of an organophosphorus ligand or an organometallic complex of rhodium and more than one type of an organophosphorus ligand;
providing a linear alpha olefin;
isomerizing said linear alpha olefin by said first catalyst in the presence of CO and H2 at a first pressure to produce an isomerized olefin; and
hydroformylating said isomerized olefin by said first catalyst in the presence of CO and H2 at a second pressure higher than said first pressure to produce a branched aldehyde.

2. The process according to claim 1, wherein said branched aldehyde is a 2-alkyl branched aldehyde.

3. The process according to claim 1, wherein said linear alpha olefin is a C4-C36 linear alpha olefin.

4. The process according to claim 1, wherein said branched aldehyde produced from a C4-C36 linear alpha olefin comprises a C5-C37 branched aldehyde.

5. The process according to claim 1, wherein said linear alpha olefin is a 1-Butene and said branched aldehyde comprises a branched Pentanal.

6. The process according to claim 1, wherein said linear alpha olefin is a 1-Hexene and said branched aldehyde comprises a branched Heptanal.

7. The process according to claim 1, wherein said linear alpha olefin is a 1-Octene and said branched aldehyde comprises a branched Nonanal.

8. The process according to claim 1, wherein said linear alpha olefin is a 1-Decene and said branched aldehyde comprises a branched Undecanal.

9. The process according to claim 1, wherein said linear alpha olefin is a 1-Dodecene and said branched aldehyde comprises a branched Tridecanal.

10. The process according to claim 1, wherein said linear alpha olefin is a 1-Tetradecene and said branched aldehyde comprises a branched Pentadecanal.

11. The process according to claim 1, wherein said linear alpha olefin is a 1-Hexadecene and said branched aldehyde comprises a branched Heptadecanal.

12. The process according to claim 1, wherein said linear alpha olefin is a 1-Octadecene and said branched aldehyde comprises a branched Nonadecanal.

13. The process according to claim 1, wherein the organophosphorous ligand can be a phosphine.

14. The process according to claim 1, wherein the phosphine ligand can be triphenylphosphine.

15. The process according to claim 1, wherein the organophosphorous ligand can be a phosphite.

16. The process according to claim 1, wherein the phosphite ligand can be tris (2, 4-di-t-butylphenyl) phosphite.

17. The process according to claim 1, wherein a mixture of organophosphorous ligands of different types can be a mixture of triphenylphosphine and tris (2, 4-di-t-butylphenyl) phosphite.

18. The process according to claim 1, wherein said first catalyst is formed when the molar ratio of phosphorous to rhodium in a range of 1:1 to 1000:1.

19. The process according to claim 1, wherein the organometallic complex of rhodium and more than one type of an organophosphorus ligand has an organophosphorous ligand which is a phosphine and an organophosphorous ligand which is a phosphite.

* * * * *